United States Patent [19]
Hansen

[11] Patent Number: 5,897,317
[45] Date of Patent: *Apr. 27, 1999

[54] DENTAL HANDPIECE WITH DISPOSABLE FILTER CARTRIDGE

[76] Inventor: James W. Hansen, 34 Mint Cir., Middleburg, Fla. 32068

[ * ] Notice: This patent issued on a continued prosecution application filed under 37 CFR 1.53(d), and is subject to the twenty year patent term provisions of 35 U.S.C. 154(a)(2).

[21] Appl. No.: 08/740,439

[22] Filed: Oct. 29, 1996

[51] Int. Cl.⁶ ........................................ A61C 1/05
[52] U.S. Cl. ............................. 433/132; 433/126
[58] Field of Search .................... 433/80, 81, 82, 433/84, 85, 86, 87, 88, 132, 126; 210/323.2, 446

[56] References Cited

U.S. PATENT DOCUMENTS

| | | | |
|---|---|---|---|
| 3,364,576 | 1/1968 | Kern, Jr. | 433/132 |
| 4,950,159 | 8/1990 | Hansen | 433/80 |
| 5,204,004 | 4/1993 | Johnston et al. | 433/80 X |
| 5,230,624 | 7/1993 | Wolf et al. | 433/82 |
| 5,234,338 | 8/1993 | Young | 433/80 |
| 5,380,201 | 1/1995 | Kawata | 433/132 |
| 5,387,339 | 2/1995 | Lee et al. | 210/326 |

*Primary Examiner*—Nicholas D. Lucchesi
*Attorney, Agent, or Firm*—Arthur G. Yeager; Earl L. Tyner

[57] ABSTRACT

Dental drill handpiece having a disposable filter cartridge for cleaning drive air, water, chip air, and exhaust passing through the handpiece.

10 Claims, 2 Drawing Sheets

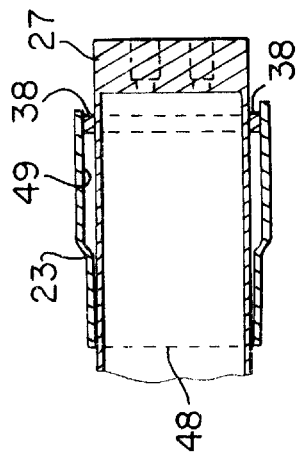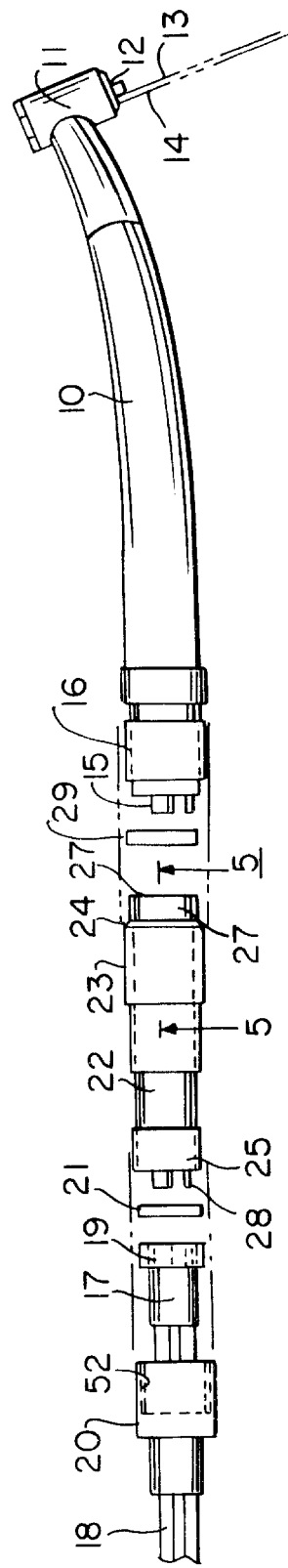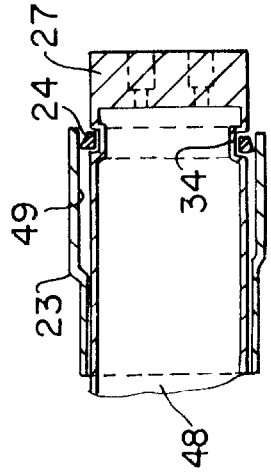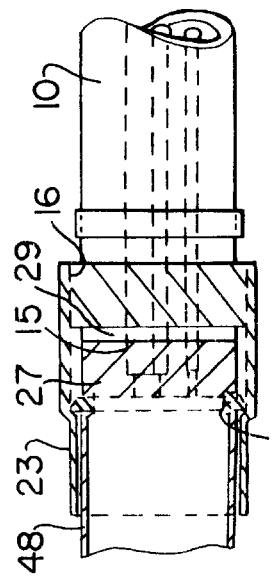

DENTAL HANDPIECE WITH DISPOSABLE FILTER CARTRIDGE

TECHNICAL FIELD

This invention relates to dental equipment, especially to dental hand drills, whether high speed or low speed, which contain passageways for air, water, and exhaust used during dental procedures; and more particularly to a disposable filter cartridge which can be inserted into the equipment to filter the air, water, and exhaust in those passageways.

BACKGROUND

Dental equipment commonly found in a dentist's office today includes a hand held instrument, such as a high speed or low speed drill which is operated by a foot pedal rheostat. The equipment includes several tubes gathered in an adaptor to connect the instrument to a source of compressed air, a source of pressurized water, and an exhaust outlet. The instrument can be easily disconnected from the tubes for cleaning purposes by way of a threaded sleeve coupler. Generally the instrument is sterilized after every use and made ready for the next patient. The water and air, however, are not always filtered to remove dirt and other contamination, and the exhaust which may contain water, air, oil, etc. is frequently open to the atmosphere.

It is an object of this invention to provide a filter cartridge which is designed to fit snugly between the instrument handpiece and the adaptor so as to filter the lines of air, water, and exhaust going to and from the handpiece. It is another object of the invention to provide an easily replaceable filter cartridge to remove dirt, bacteria, and the like from the lines leading to the handpiece. Still other objects will become apparent from the more detailed description which follows.

BRIEF SUMMARY OF THE INVENTION

This invention relates to a dental handpiece having internal passageways to deliver air to drive the handpiece drill chuck, bit water to cool the drill bit, chip air, and an exhaust to carry air away from the drill to a disposal location. This invention provides a filter cartridge having three longitudinal separate cavities containing filter media to remove particles and/or bacteria as small as about 0.2 microns, the cartridge being joinable to the internal passageways in the handpiece so as to filter the flow of air, water, and exhaust through the handpiece. An adaptor is employed to allow the filter cartridge to be easily replaced when a clean cartridge is needed.

In a specific and preferred embodiment a gasket is included between the handpiece and the filter cartridge as well as between the filter cartridge and the adaptor; and the filter cartridge is joined to the handpiece and to the adaptor by means of a threaded sleeve coupler at each connection. It is especially advantageous that the filter cartridge is easily replaceable by hand, without and special tools.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is an exploded side elevational view of a dental handpiece employing the filter cartridge of this invention;

FIG. 5 is a cross sectional view taken at 5—5 of FIG. 1;

FIG. 6 is a cross sectional view similar to FIG. 5, but with the connection between the handpiece and the filter closed; and FIG. 7 is a cross-sectional view similar to that of FIG. 5, but showing an alternative embodiment in the ledge needed to cooperate with a sliding sleeve in assembling the cartridge into the handpiece.

DETAILED DESCRIPTION OF THE INVENTION

Figure 3:
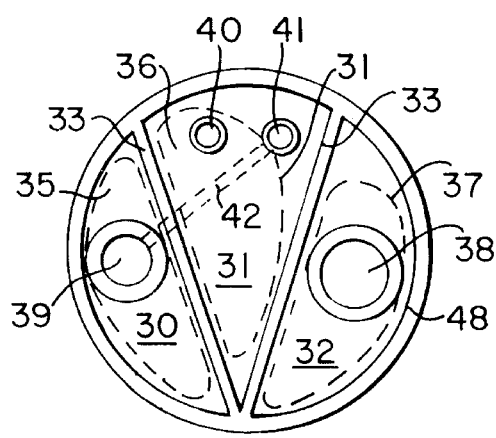
FIG. 3 is a top plan view of the filter cartridge of FIG. 2.

The features of this invention are best understood by reference to the attached drawings showing numbered components.

The invention is a combination of three components that fit snugly together with the help of two gaskets. The three components are a dental handpiece 10, an adapter 17, and a filter cartridge 22. When these three components are fastened together with gaskets 21 and 29, there is a single unitary structure for the dentist to use, including air, water, and exhaust lines.

In the prior art handpiece 10 is connected directly to adapter 17, and there is no filter between the two. The handpiece 10 has a drill head 11 from which projects the end of a chuck 12 which holds a slender bur which spins at a high speed and grinds away portions of a tooth. In order to keep the bur cool a small spray 13 of water is directed at the bur head. In addition a small spray 14 of air (called "chip air") is directed at the bur head to blow away chips of tooth that may obscure the dentist's vision. This chip air can also be mixed with water to give a spray mist. The bur is driven by a miniature turbine system which is operated by a stream of air (called "drive air"). All of these components namely, drive air, chip air, and water are turned on and off by foot pedals operated by the dentist. There is also an exhaust return line from the handpiece head sending air and possibly small droplets of oil and water, to the room atmosphere or to the dental unit. This is principally necessary to provide an exit for the drive air after it leaves the turbine. All of these functions are provided by tubes 18 which pass through the adaptor 17 and the handpiece 10 to the drill head 11. The handpiece 10 and the adaptor 17 are separable for cleaning and repair by way of a male-female coupling which includes protruding tube ends 15 (normally made of metal or plastic) which mate with recesses in the female coupler head 27 of cartridge 22. A gasket 29 with holes for the tube ends 15 to pass through is included for a tight connection. The tightness of the connection is accomplished by a sliding sleeve coupler 23 having internal threads at 49 to engage external threads at 16 on handpiece 10. Thus, the prior art provided a fully operational dental handpiece to include drive air, chip air, water, and exhaust. The prior art, however, failed to provide appropriate cleanliness. The air lines carried moisture, bacteria, and dust; the water lines included particles of bacteria and dirt; and the exhaust line carried air, possibly including some water, dirt, bacteria, and oil directed to the atmosphere in the same room where the patient was being treated. No attempt was made to keep these lines clean. Applicant has invented a filter for a dental syringe (See U.S. Pat. No. 4,950,159) but there has not been previously available a dental handpiece used for drilling and fitted with a filter to remove dirt and bacteria from the lines providing air and water thereto.

In the present invention a filter cartridge 22, a gasket 29 and a sliding sleeve coupler 23 are added to the system so as to filter out dirt and bacteria from the air and water, and to clean up the exhaust.

This invention does not require a change in the structure or design of the handpiece 10 of the prior art in order to employ the present invention; and similarly, there is no change in the structure of the adaptor 17 from the prior art use to the present use. The entire improvement lies in the filter cartridge 22, the gasket 29 and the sliding sleeve coupler 23 employing a snap ring or an equivalent ledge on the cartridge 22.

Figure 2:
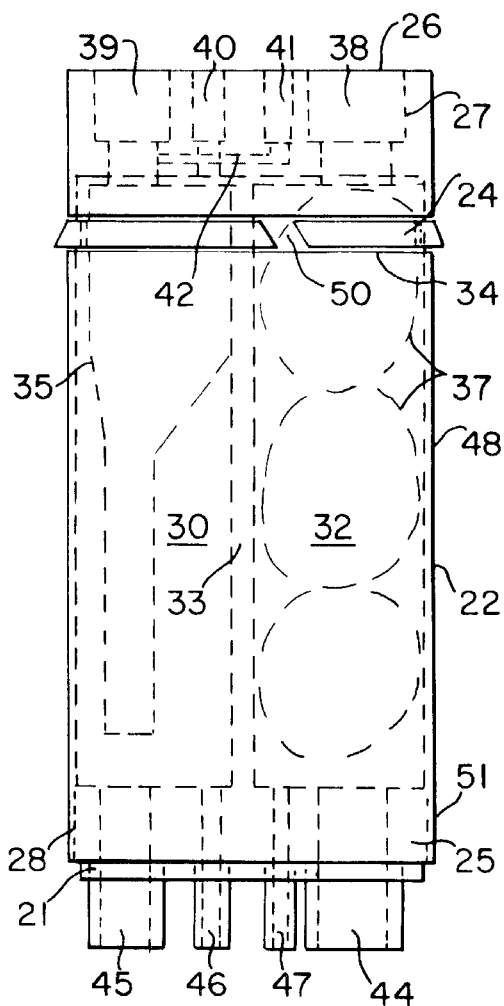
FIG. 2 is a front elevational view of the filter cartridge of this invention.
Figure 4:
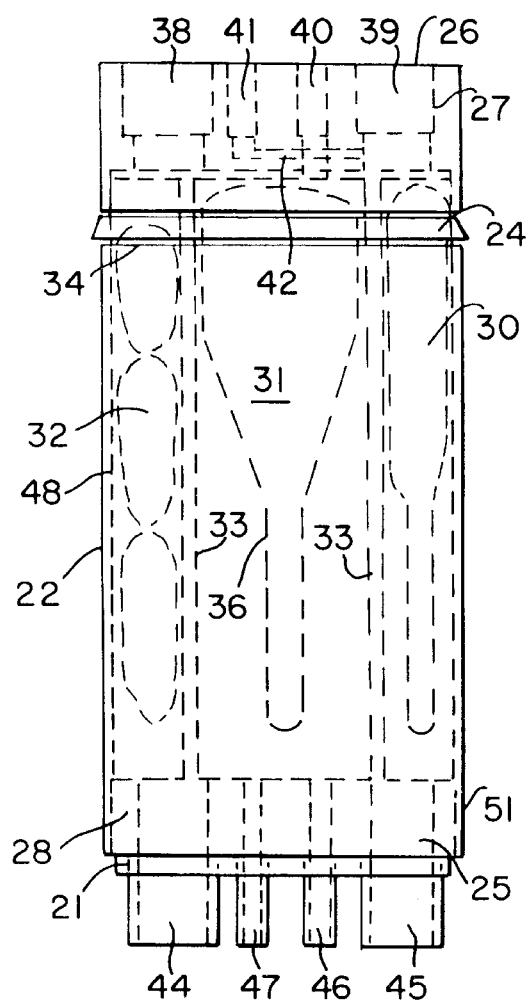
FIG. 4 is a rear elevational view of the filter cartridge of FIGS. 2 and 3.

FIGS. 2–6 show the details of the filter cartridge 22. Gasket 29 is similar to gasket 21; and sliding sleeve coupler 23 is similar to sliding sleeve coupler 20. The principal improvement lies in the filter cartridge 22 illustrated in FIGS. 2–6.

It may be seen that filter cartridge 22 is a hollow cylindrical structure comprising a body 48 with a proximal end 25 connectable to the adapter 17 and a distal end 26 connectable to the handpiece 10. Body 48 has a solid female coupler head 27 at distal end 26 and a solid male coupler head 28 at proximal end 25. The remainder of body 48 between heads 27 and 28 is divided by walls 33 into three hollow cavities 30, 31 and 32. These three cavities may be the same or different in volume, depending on the design, although generally they will be approximately equal in volume. Cavity 30 as shown herein is employed to receive a filter 35 for filtering drive air. Passageway 42 connects counterbored hole 39 to counterbored hole 41 so as to provide filtered air from cavity 30 to the inlet of chip air to be directed at the bur of the handpiece 10 as mentioned above. Cavity 31 as shown herein is employed to receive filter 36 to filter the water. Cavity 32 as shown herein is employed to receive filter 37 to filter the exhaust. Filters 35 and 36 are the most important of the three filters in this invention, since it is important to filter out dirt and any other type of particle, e.g., bacteria, which may be introduced into the patient's mouth during the dental procedures to which the patient is subjected. Generally filters 35 and 36 may be fibrous materials or particulate materials which are small enough to be capable of filtering out particles down to about 0.2 microns in size, which is generally small enough to include bacteria. Materials found to be useful for this purpose are polyolefins, cellulosic materials, resins fibrous materials treated with resins, gels, filter media coated with or sprayed with a bactericide, and the like. It is not the purpose of this invention to be limited by the type of filter media used, since some may be better than others. In general, however, the filters 35 and 36 must be capable of removing particles as small as 0.2 microns in size. Filter 37 is not so critical as filters 35 and 36, since the former filters the exhaust of the dental handpiece, which generally includes water mist and tiny droplets of oil, and ordinary filter media such as cotton, carbon particles, etc. are capable of removing these contaminants.

Female coupler head 27 is a solid disc with counterbored holes 38–41, each of which is adapted to receive the male protruded tube ends 15 (see FIG. 1) of the handpiece 10. Coupler head 27 is an integral part of cartridge 22. The tube ends 15 are plastic or metal, stainless steel preferably, to which are connected tubes leading to drill head 11. Tube ends 15 are firm and inflexible so as to be easily plugged into the corresponding recesses in female coupler head 27 in the same manner that an electric plug is connected to a wall outlet. Female coupler head 27 has a large bore in each recess 38–41 to receive the corresponding tube end which will seat itself at the shoulder of the large bore. Each tube end is a tube with a central hollow for conducting the fluid on to its destination, and the small bore of each recess 38–41 is a portion of the conduit for the air, water or exhaust.

At proximal end 25 the male coupler head 28 is fashioned the same as the tube ends 15 which protrude from handpiece 10. Tube ends 44–47 are preferably molded plastic integrally molded as part of body 48 when cartridge 22 is molded of that plastic. Tube ends 44–46 are sized so as to plug into corresponding recesses in female coupler head 19 of adapter 17. A gasket 21 is shown (similar to gasket 29) which is compressed to provide a leakproof fit when adapter 17 is tightened against filter cartridge 22. Adjacent the proximal end 25 of cartridge 22 are external screw threads 51 to engage sliding sleeve coupler 20 having internal threads 52. By tightening sleeve coupler 20 adapter 17 is pressed against gasket 21 which in turn is pressed against proximal end 25 of filter cartridge 22.

It may be seen that counterbore 38 for exhaust appears to be larger than counterbore 39 for drive air, and counterbores 40 and 41 are both very small and about equal in size. These relative sizes are generally preferred. Drive air through counterbore 39 is controlling. The volume of water through counterbore 40, and the volume of chip air through counterbore 41 are both relatively small.

As seen in FIGS. 5, 6, and 7 the filter cartridge also carries a sliding sleeve coupler 23 for attachment to the external threads 16 on handpiece 10. In order for sleeve coupler 23 to have a ledge on filter cartridge body 48 to allow the tight coupling to be made, there may be a ledge fashioned on body 48. If body 48 is a molded plastic container a ledge 38 may be molded thereon as shown in FIG. 7. Alternatively, a groove 34 may be molded on body 48 adjacent distal end 26 of the cartridge 22 as shown in FIGS. 5 and 6. In groove 34 there is placed a loosely fitting snap ring 24, which is split such as at 50, so as to permit ring 24 to be expanded enough to slip over the outside of body 48 and engage itself in groove 34. The cross section of ring 34 is of a shape and size to prevent the smaller portion of sleeve coupler from sliding by, and thereby provide a means for tightening handpiece 10 to filter cartridge 22 with gasket 29 therebetween. The shape of ring 34 generally slopes outwardly as shown in FIGS. 2, 4, 5 and 6 so as to permit initial assembly of ring 34 to cartridge 22 by sliding it downward around cartridge 22 and passing ring 34 by compressing the split 50 together momentarily.

In the manufacture of cartridge 22 it may be convenient to make the cartridge body 48 in two pieces that can be attached to each other by adhesive connection or by welding (heat softening). This procedure might facilitate the loading of filters 31, 35 and 37. The cartridge body 48 could be molded in two pieces that have a juncture plane transverse to the lengthwise direction of body 48 with tongue-and groove joints for joining the two portions, after loading the cavities with filters, into one structure. Of course, there are other arrangements that might be employed to manufacture cartridge 22 when body 48 is a molded plastic material. It is within the scope of this invention to provide optical fibers leading from a battery operated light bulb to an outlet in the handpiece head so as to provide illumination inside the patient's mouth.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what it is desired to secure by Letters Patent of the United States is:

1. A dental drill comprising a handpiece containing a means for securing a drill bit thereto, said handpiece having internal passageways to deliver compressed air to drive said drill bit, to deliver water to cool said drill bit, to deliver chip air to blow tooth chips away, and to carry exhaust air away from the drill bit to a dental disposal unit, a supply adapter separately joinable to said handpiece and including tubes for conducting air, water, and chip air to said handpiece and an exhaust to remove exhaust air from said handpiece; and a filter cartridge having three longitudinal separate cavities containing fibrous filter media for filtering incoming streams of air, chip air, and water and an outgoing stream of exhaust air; said cartridge being separably joinable to said handpiece at one end of said cartridge and separably joinable to said adapter at the other end of said cartridge; said filter media for incoming air, water, and chip air being capable of removing therefrom all solid materials having a size of at least 0.2 microns.

2. The system of claim 1 which additionally includes a gasket between said cartridge and said handpiece and a gasket between said cartridge and said adapter.

3. The system of claim 1 which additionally includes a threaded sleeve coupler to join the cartridge to the handpiece and the cartridge to the adaptor.

4. The system of claim 1 wherein the coupling of said handpiece to said cartridge and the coupling of said cartridge to said adaptor comprises protruding tubular portions that fit snugly into corresponding recesses in a male-female connection.

5. The system of claim 1 wherein said cartridge has a proximal end joined to said adaptor and a distal end connected to said handpiece; said proximal end having male protruding tubing portions to join to said tubes in said adaptor, and has female recesses at said distal end to receive male protruding tubes from said handpiece; said cartridge having external screw threads to engage internal threads on a sleeve coupler slidingly attached to said adaptor and said cartridge having at its distal end a sliding sleeve coupler with internal screw threads to engage external threads on said handpiece.

6. The system of claim 5 wherein said cartridge includes adjacent said distal end a split snap ring contained in an encircling groove around the outside of said cartridge; said snap ring being a stop member engaging said sleeve coupler to prevent it from sliding off said distal end.

7. The system of claim 1 wherein said cartridge includes adjacent said distal end an outwardly protruding ledge to function as a stop member engaging said sleeve coupler.

8. A filter cartridge tor attachment in line between an adaptor having respective tubes of drive air, water, chip air and exhaust and a dental drill having an elongated handpiece containing a means for securing a drill bit thereto and internal passageways for drive air, water, chip air and exhaust, said cartridge comprising an elongated housing having a proximal end and a distal end and being adapted to be inserted between the dental handpiece and the adaptor, said housing of said filter cartridge being separably joinable to the adaptor at said proximal end and separably joinable to the handpiece at said distal end; said housing having three internal lengthwise separate cavities, each said cavity containing filter material, a first of said cavities and its filter material adapted to be connected so as to filter incoming drive air through the adaptor, a second of said cavities and its filter material adapted to be connected so as to filter incoming water through the adaptor; and a third of said cavities and its filter material adapted to be connected so as to filter outgoing exhaust through the adaptor; said filter material in said first and second cavities being capable of filtering solids having a size of 0.2 microns or larger.

9. The filter cartridge of claim 8 which additionally includes a suitable gasket at each proximal and distal end thereof, a split snap ring encircling said cartridge in a groove adjacent the distal end thereof, and a slidable sleeve coupler contained by said snap ring and having internal threads to engage external threads on said handpiece.

10. The filter cartridge of claim 1 in which said filter material for incoming air and water is selected from the group consisting of fibrous cotton, fibrous polyolefin, carbon powder, resin, resin-treated fibrous materials and any of said filter material treated with a bactericidal composition.

\* \* \* \* \*